United States Patent [19]
Mraz

[11] Patent Number: 5,766,373
[45] Date of Patent: Jun. 16, 1998

[54] METHOD AND APPARATUS FOR DETERMINING THE DOUBLING OF THE VOLUME OF RISING DOUGH

[76] Inventor: David M. Mraz, 155 Manor Dr., Mill Valley, Calif. 94941

[21] Appl. No.: 615,017

[22] Filed: Mar. 12, 1996

[51] Int. Cl.[6] .............................. A21D 6/00; G01F 7/00
[52] U.S. Cl. ........................ 426/231; 426/496; 73/169; 73/319
[58] Field of Search ............................ 426/231, 490; 73/169, 319, 309, 322

[56] References Cited

U.S. PATENT DOCUMENTS

| | | |
|---|---|---|
| 1,654,897 | 1/1928 | Rosemblum . |
| 4,467,645 | 8/1984 | Weir ........................................ 73/215 |
| 4,565,703 | 1/1986 | Garbar . |

FOREIGN PATENT DOCUMENTS

| | | |
|---|---|---|
| 134988 | 11/1929 | Sweden . |
| 193286 | 2/1923 | United Kingdom . |

OTHER PUBLICATIONS

Carol field,"Focaccia: Simple Breads from the Italian Oven", p. 27, 1994.

*Primary Examiner*—Deborah Yee
*Attorney, Agent, or Firm*—Flehr Hohbach Test Albritton & Herbert

[57] ABSTRACT

Method and apparatus for determining the doubling in volume of a rising dough includes a horizontal beam placed across the edge of the bowl which has a retaining notch for a vertical calibrated stick whose end is placed on the top of the dough to ascertain its volume either in an unrisen or risen condition. Since the bowl has nonvertical or sloping sides, the measuring stick is calibrated with a nonlinear scale to compensate or to correspond to the sloping sides. Thus the measuring stick has marked on its scale, for example, the number of cups of dough in the bowl. A measurement is initially made before the dough has risen and then doubled to provide the user with a measurable number which periodic checking will indicate when the dough has increased to that desired volume.

8 Claims, 3 Drawing Sheets

5,766,373

1

METHOD AND APPARATUS FOR DETERMINING THE DOUBLING OF THE VOLUME OF RISING DOUGH

The present invention is directed to a method and apparatus for determining the doubling of the volume of rising dough, and more specifically when a bowl with sloping or nonvertical sides is used.

BACKGROUND OF THE INVENTION

In the baking field the rising of dough from the process of fermentation with yeast is usually accompanied with the baking directions such as "let rise until doubled about xx minutes". The home baker fears these words because of the potential variables of the yeast-baking process which are: ambient temperature and humidity, variation with ingredients (i.e., organic stone ground flour to high speed steel-milled flour, and various yeasts), variable temperatures with the yeast and reliable ingredient measurement. The real desired measurement for the rising of dough is the measure of its volumetric expansion. Most mixing bowls have sloped or curved or nonlinear sides as, for example, shown in the Rosenblum U.S. Pat. No. 1,634,897, a measuring technique has been proposed which uses a vertical measuring stick with a linear scale and an automatic alarm. However this scale does not accommodate the sloping sides of the bowl. It is apparent that this instrument of Rosenblum is for professional bakers since the patent states on page 3, starting at line 85, "the device can be readily set at any desired elevation for the different steps of fermentation according to the experience or judgment of the baker and varying according to the different dough he is making." And then in the final sentence, the patent states "Heretofore it has been very difficult to attain such uniformity even after a baker had produced several batches of desired character of bread."

In order to simplify the measurement of the volumetric rising of a dough, in a modern day cookbook, for example, by Carol Field, entitled "Focaccia—Simple Breads from the Italian Oven", published in 1994, she suggests using a "straight-sided translucent plastic container" such as a two-quart Pyrex measuring cup (which already has linear gradations on it). And the book states "This allows you to mark the side where the dough starts to rise. It is then easy to monitor the process and know exactly when the dough has doubled." To accomplish this you must buy the special container and lightly oil the sides and, of course, transfer the dough from your ordinary slope-sided mixing bowl. This is very inconvenient.

OBJECT AND SUMMARY OF THE INVENTION

An object of the present invention is to provide an improved method of determining the doubling in volume of a rising dough.

In accordance with the above object, a method of determining the doubling in volume of a rising dough, or some predetermined increase in volume, in a bowl with sloping or nonvertical sides comprising the steps of providing a volumetrically calibrated measuring stick having a nonlinear scale corresponding to the nonvertical sides.

The dough is formed which will rise in a nominal time period to double its volume or a predetermined increase in volume in the bottom of the bowl. The end of the calibrated stick vertically oriented and placed on top of the unrisen dough and its scale referenced with a fixed horizontal level for indicating the volume of the unrisen dough in said bowl. The dough is allowed to rise to twice or to a predetermined

2 greater volume. The volume of such rising is determined by placing the end of the calibrated stick on top of the risen dough and comparing its scale to the fixed horizontal level.

Additionally apparatus is provided which includes a horizontal support beam which may be horizontally laid across the top edge of the bowl having horizontal level reference indicator, including means for movably retaining the elongated member in the vertical orientation. Then the calibrated measuring stick is retained by and vertically slidable in the retaining means.

DETAILED DESCRIPTION OF PREFERRED EMBODIMENTS

Figure 1:
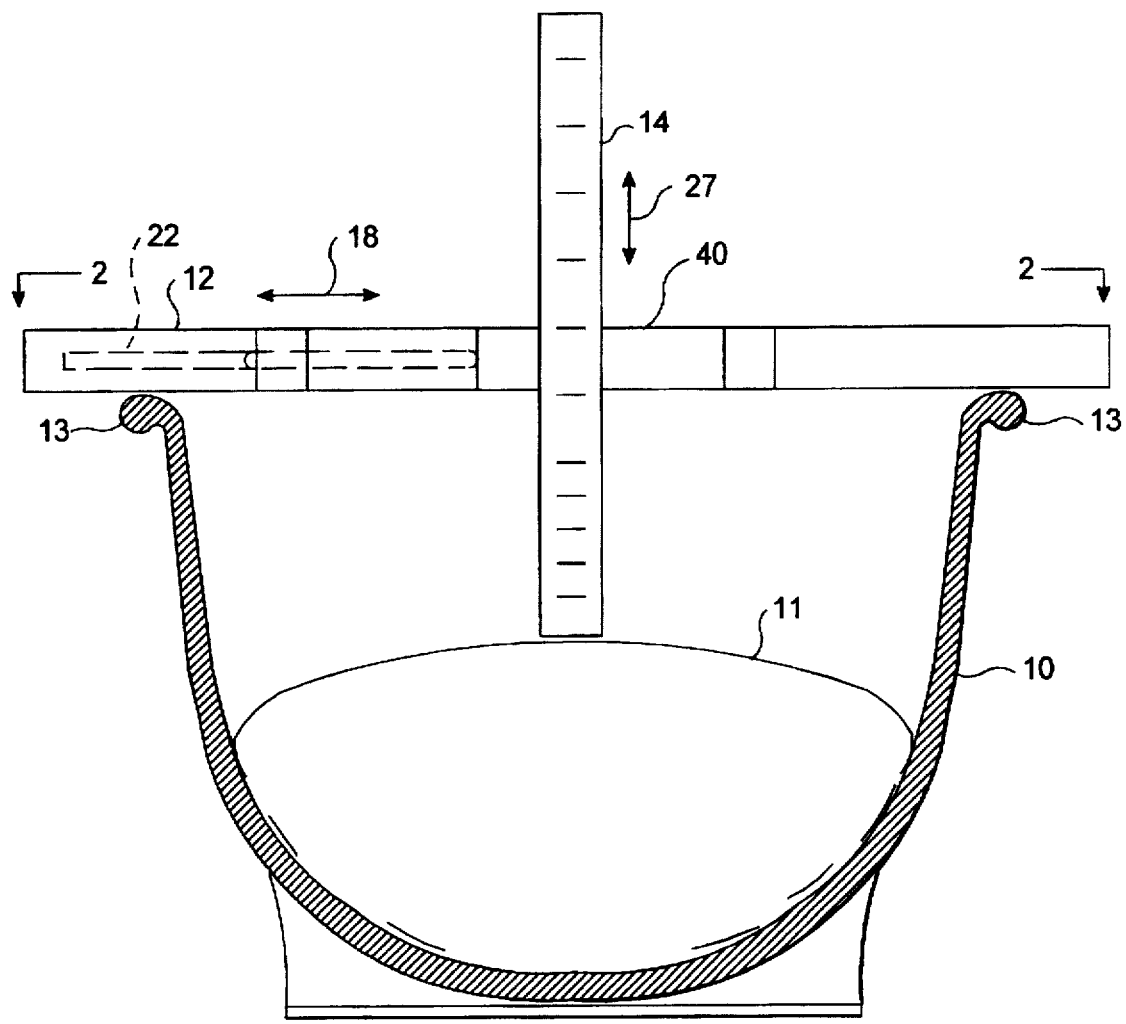
FIG. 1 illustrates the method and apparatus of the present invention in a dough that has doubled its volumetric size and is a cross sectional view of the bowl in which the dough is placed.

FIG. 1 illustrates a typical mixing bowl 10 found in the home in which a lump of bread dough 11 has been mixed and allowed to rise to approximately double its volume as illustrated in FIG. 1. Referring to FIG. 3, the dough 11' in its unrisen state is illustrated in the same bowl 10.

Figure 2:
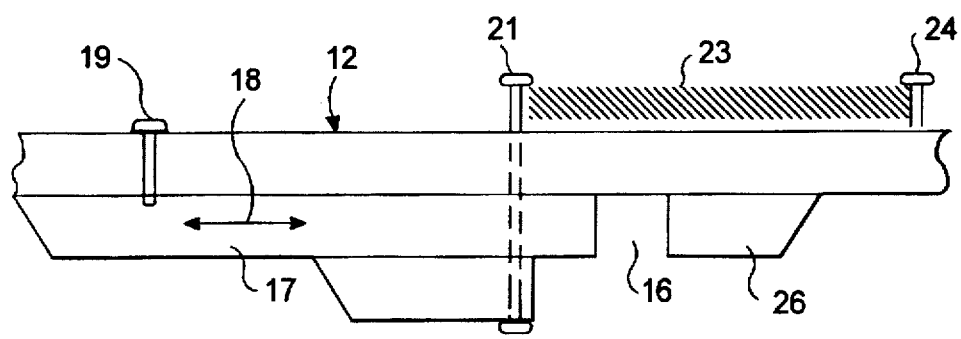
FIG. 2 is a top plan view taken along the line 2—2 of FIG. 1 eliminating the bowl and the vertical calibrated measuring stick.

To measure the volume of the risen bread dough 11, there is provided measuring apparatus which comprises a horizontal beam 12 which is placed across the top edge 13 of the bowl, and which retains, so that it is vertically slidable, a calibrated measuring stick 14. FIG. 2 shows the beam 12 and the square notch 16 in which the measuring stick 14 is slidably retained. This is accomplished by the slider unit 17 which slides in the direction shown by the double arrow 18 and is retained on the main part of the beam 12 by a pair of fasteners 19 and 21, both of which slide in the channel 22 in beam 12 (see also FIG. 1). Also fastener 21 has a spring 23 attached to another fastener 24 on the beam 12 to bias slide 17 against the calibrated stick 14 and the raised abutment 26 which is fixed beam 12. Other techniques of slidably retaining stick 14 are obviously available including ratcheting the stick. The vertical slidability of stick 14 is indicated by the double ended arrow 27.

Figure 4:
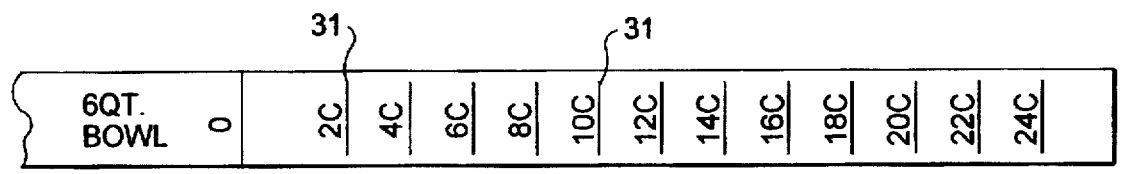
FIG. 4 is a plan view of the measuring stick shown in FIGS. 1 and 3.
Figure 3A:
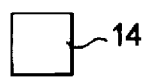
FIG. 3A is top view of the measuring stick of FIG. 3.
Figure 3:
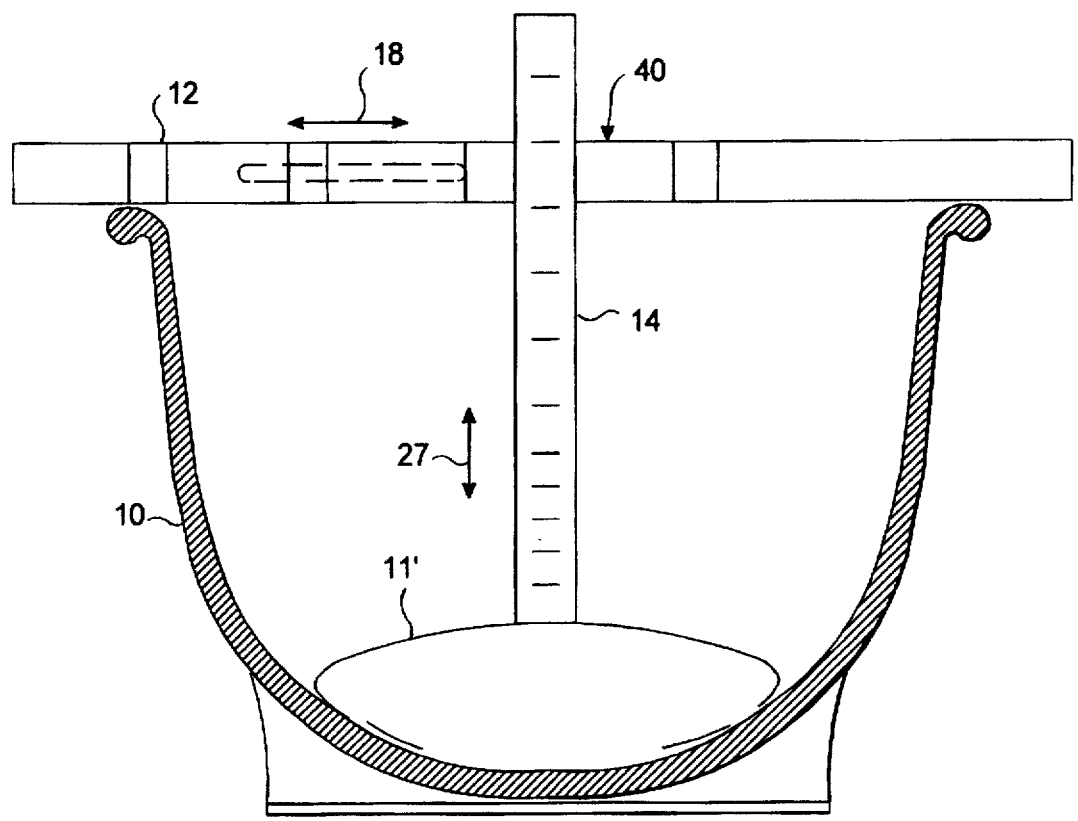
FIG. 3 is a cross sectional view similar to FIG. 1 showing the dough in its original unrisen state.

Typically as illustrated in FIG. 3A, the calibrated stick 14 has a square cross section. This serves two purposes. First as illustrated in FIG. 4 on each face of the stick, a separate calibrated scale may be installed which is applicable to a specific type of bowl. For example, in FIG. 4 it is a six-quart bowl which, for example, might have the shape of bowl 10. Since the bowl has sloping or nonvertical sides, the scale indicated by the lines 31 of FIG. 4 are nonlinear; that is, since the bottom of the bowl is narrower, the lines from 0 to 2C (indicating two cups) and 4C are wider apart than those at the top which correspond to the measuring stick touching the dough as it has risen towards the top of the bowl. The second reason for the square stick 14 is to provide a flush surface with the face, for example, of abutment 26 as illustrated in FIG. 2 so that if a new bowl is used for which a new calibrated stick must be made, the user can usually write on the face of the stick during the calibration procedure. And such procedure is illustrated in FIG. 5.

Figure 5:
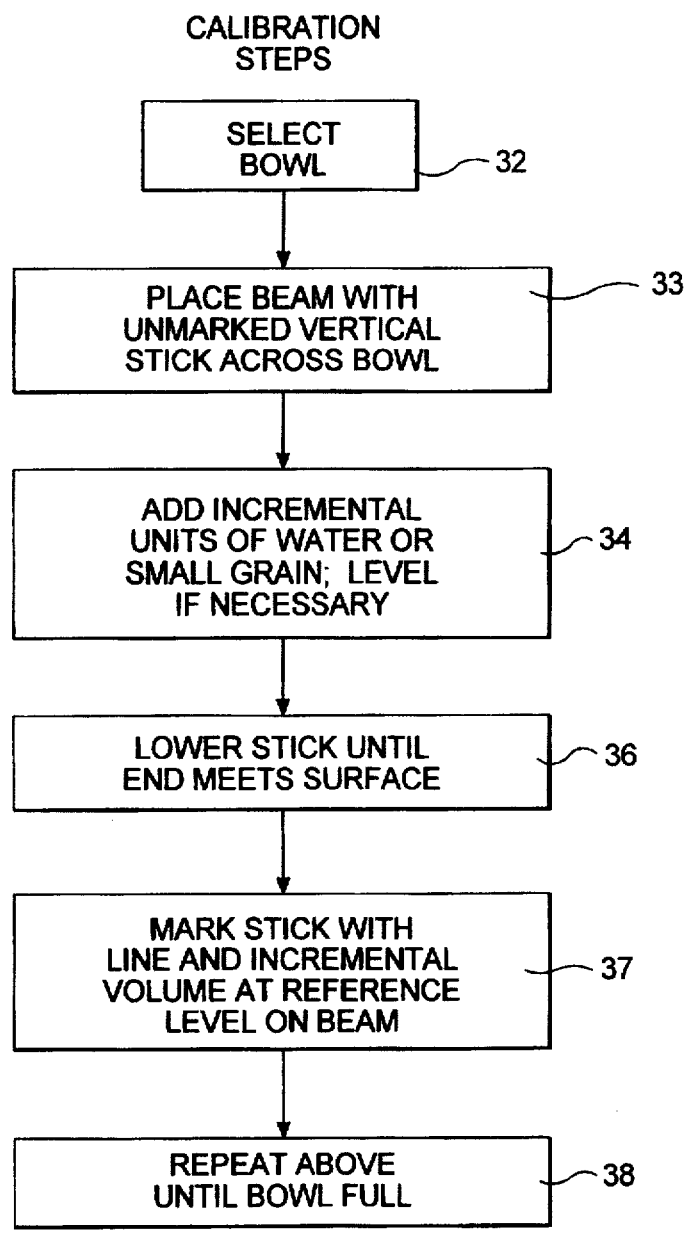
FIG. 5 is a flow chart illustrating the method of the present invention.

Referring to the calibration steps of FIG. 5, this would be applicable in the case where a new type of bowl is used where the existing calibrations supplied the user are not applicable. In other words, from a marketing standpoint, the user is sold a product which consists of one beam with a clamp device and a set of calibrated sticks. The calibrated sticks will have frequent calibrations which will be applicable to well known classic bowl shapes and mixers and others will remain blank for custom calibration by the user. Thus for a custom calibration the user as illustrated in Step 32 selects a bowl. In Step 33 the beam is placed across the bowl with the unmarked vertical stick in the bowl.

As illustrated by Step 34, incremental units of water or small grains such as rice or wheat are used as a calibration medium. If necessary the surface is leveled. Next in Step 36 the stick is lowered until the end of the stick meets the surface, as shown, for example, in FIGS. 1 and 3. In Step 37 the stick is marked with a line and the incremental volume. This is done at the level provided by beam 12 which may nominally be the top of the beam for example shown at 40. Thus as illustrated in FIG. 4, besides the scale line 31, the volume is written; in FIG. 4 it is shown in cups but the increments could be half cups or whatever is desired. Also, of course, metric measurements are suitable such as milliliters. Finally in Step 38 the incremental amounts of water or grain are added until the bowl is almost full. Referring to FIG. 4 this would be the 24-cup point. Thus by the foregoing technique the measuring stick is calibrated to form a nonlinear scale which corresponds to the nonvertical or sloping sides of that particular bowl for which it is applicable.

Figure 6:
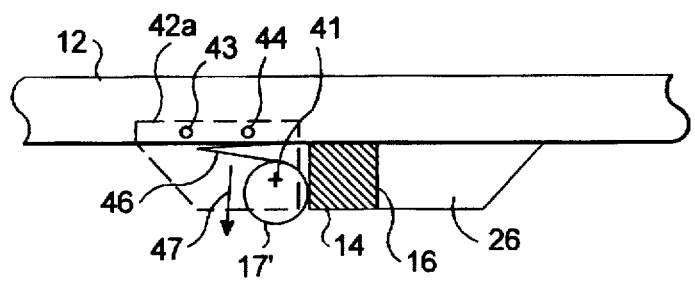
FIG. 6 is a top plan view similar to FIG. 2 but showing an alternative embodiment.

FIG. 6 shows an alternative to the stick retaining means of FIG. 2 in that rather than using a linear spring-loaded slider 17, a roller 17' is used which is off-center mounted as indicated at 41 on a pair of plates 42a, b, only one of which is shown in dashed outline. The plates 42a, b are fixed to the beam 12 by the pins 43 and 44. The lease spring 46 provides a spring pressure illustrated by the vector 47 to normally bias the roller 17' against stick 14. By either use of a finger or lever (not shown) to push the roller back toward the beam against the pressure of the spring, the stick 14 may be released.

Now referring to the actual process and use of the measuring device after a suitable calibrated stick has been obtained, first the baker forms the dough, mixes it and softly pats the dough surface roughly level, as shown in FIG. 3. A measurement is taken with using the reference level 40 as illustrated in FIG. 3 with the end of the stick 14 just touching the surface. This measurement is recorded as well as the clock time. When the rising of the dough becomes evident, other measurements are taken periodically until the dough has doubled or risen according to the recipe. Again the clock time is noted and the elapsed time compared only as matter of interest for future use. The risen dough may have somewhat of a shallow convex surface. If there is too much slope, then the measurement can be taken off center as in the risen dough of FIG. 1 by the moving beam 12 to provide an estimate representative of the risen level. However, this may be merely a second order effect. The number of cups read off of the calibrated stick 14 at the reference level 40 should be double the original number assuming that the recipe provides for doubling of the dough.

Because of the symmetrical design of the beam 12 it may easily be used as described above by left as well as right handed individuals. Specifically by merely turning the beam end to end stick retainer slider 17 or the off-center roller 17' may easily be manipulated by a desired hand.

Thus an improved method of determining the doubling in volume of a rising dough and apparatus has been provided.

What is claimed is:

1. A method of determining the doubling in volume of a rising dough, or some predetermined increase in volume, in a bowl with sloping or nonvertical sides comprising the following steps:

for that particular bowl providing a volumetrically calibrated measuring stick having a nonlinear scale corresponding to said nonvertical sides;

forming dough which will rise in a nominal time period to double its volume or a predetermined increase in volume in the bottom of said bowl;

vertically orienting and placing the end of said calibrated stick on top of said unrisen dough and referencing said scale with a fixed horizontal level for indicating the volume of said unrisen dough in said bowl;

allowing said dough to rise to twice or to a predetermined greater volume;

and determining the volume of such rising by placing the end of said calibrated stick on top of said risen dough and comparing its scale to said fixed horizontal level.

2. A method as in claim 1 including the step of calibrating said stick by pouring cups of water or some similar liquid-like granular material into said bowl, vertically orienting the end of said stick at the level of said water or material, and marking the number of cups or volume measurement on the stick to form said nonlinear scale.

3. Apparatus for determining the doubling in volume of a rising dough, or some predetermined increase in volume, in a bowl with sloping or nonvertical sides comprising:

a horizontal support beam which may be horizontally laid across the top edge of such bowl and having a horizontal reference level indicator and also including means for movably retaining an elongated member in a vertical orientation;

a calibrated measuring stick having a nonlinear scale which is volumetrically calibrated to correspond to the volume of the material in said bowl when the stick is vertically placed with its end on the top of such dough, said nonlinear scale corresponding to the nonvertical or sloping sides of said bowl, said calibrated stick being retained by and vertically slidable in said retaining means of said horizontal beam.

4. Apparatus for determining the doubling in volume of a rising dough, or some predetermined increase in volume, in a bowl with sloping or nonvertical sides comprising:

a horizontal support beam which may be horizontally laid across the top edge of such bowl and having a horizontal reference level indicator and also including means for movably retaining an elongated member in a vertical orientation;

a measuring stick which may be calibrated with a nonlinear scale which is volumetrically calibrated to correspond to the volume of the material in said bowl when the stick is vertically placed with its end on the top of such dough, said nonlinear scale corresponding to the nonvertical or sloping sides of said bowl, said calibrated stick being retained by and vertically slidable in said retaining means of said horizontal beam;

said stick being calibrated by pouring cups of water or some similar liquidlike granular material into said bowl, vertically orienting the end of said stick at the level of said water or material, and marking the number of cups or volume measurement on the stick to form said nonlinear scale.

5. Apparatus as in claim 3 where said retaining means allows said stick to be marked on its surface for calibration.

6. Apparatus as in claims 3 or 5 where said stick is four sided to allow a scale to be placed on each side.

7. A method as in claim 1 where said fixed horizontal level is a beam laid across the top edge of said bowl, such beam vertically and slidably retaining said calibrated stick.

8. Apparatus as in claim 4 where said retaining means includes an off-center mounted roller, spring biased against said stick.

* * * * *